(12) United States Patent
Zalameda et al.

(10) Patent No.: US 10,605,783 B2
(45) Date of Patent: Mar. 31, 2020

(54) SYSTEM AND METHOD FOR PROGRESSIVE DAMAGE MONITORING AND FAILURE EVENT PREDICTION IN A COMPOSITE STRUCTURE

(71) Applicant: U.S.A., as represented by the Administrator of the National Aeronautics and Space Administration, Washinton, DC (US)

(72) Inventors: Joseph N. Zalameda, Poquoson, VA (US); Eric R. Burke, Yorktown, VA (US); Michael R. Horne, Yorktown, VA (US); Eric I. Madaras, Yorktown, VA (US)

(73) Assignee: UNITED STATES OF AMERICA AS REPRESENTED BY THE ADMINISTRATOR OF NASA, Washington, DC (US)

( * ) Notice: Subject to any disclaimer, the term of this patent is extended or adjusted under 35 U.S.C. 154(b) by 173 days.

(21) Appl. No.: 15/238,164

(22) Filed: Aug. 16, 2016

(65) Prior Publication Data
US 2017/0052150 A1 Feb. 23, 2017

Related U.S. Application Data

(60) Provisional application No. 62/315,363, filed on Mar. 30, 2016, provisional application No. 62/207,593, filed on Aug. 20, 2015.

(51) Int. Cl.
*G01N 29/14* (2006.01)
*G01N 1/00* (2006.01)
(Continued)

(52) U.S. Cl.
CPC .............. *G01N 29/14* (2013.01); *G01L 1/00* (2013.01); *G01N 21/8803* (2013.01);
(Continued)

(58) Field of Classification Search
CPC ................................................ G01L 1/25–255
(Continued)

(56) References Cited

U.S. PATENT DOCUMENTS 5,287,183 A * 2/1994 Thomas ................. H04N 5/217
348/571
5,798,458 A * 8/1998 Monroe ............. B64D 45/0015
360/5

(Continued)

OTHER PUBLICATIONS

Gribbon et al, A Real-time FPGA Implementation of a Barrel Distortion Correction Algorithm with Bilinear Interpolation, Nov. 2003.*

(Continued)

*Primary Examiner* — Randy W Gibson
*Assistant Examiner* — David L Singer
(74) *Attorney, Agent, or Firm* — M. Bruce Harper; Robin W. Edwards; Helen M. Galus

(57) ABSTRACT

A system for monitoring damage progression in a composite structure includes a load sensor, acoustic emission sensors, a camera, and a monitoring device. The load sensor measures an applied load to the structure. The sensors measure acoustic emission data indicative of possible damage to the structure. The camera captures image data of the structure in a designated portion of the electromagnetic spectrum. The monitoring device executes a method by which the acoustic emission data is synchronously collected with the image data and the applied load. The device automatically maps the acoustic emission data onto the image data to detect an area of damage progression in the composite structure. A failure event in the detected area of damage progression may be predicted using the mapped data, and a control action may be executed in response to the predicted failure event.

17 Claims, 3 Drawing Sheets

(51) Int. Cl.
*G01N 29/06* (2006.01)
*G01N 29/04* (2006.01)
*G01N 21/88* (2006.01)
*G01L 1/00* (2006.01)

(52) U.S. Cl.
CPC ......... *G01N 29/043* (2013.01); *G01N 29/069* (2013.01); *G01N 2291/0231* (2013.01); *G01N 2291/0258* (2013.01); *G01N 2291/106* (2013.01); *G01N 2291/2694* (2013.01)

(58) Field of Classification Search
USPC .......................................... 73/587, 801, 802
See application file for complete search history.

(56) References Cited

U.S. PATENT DOCUMENTS

| | | | | |
|---|---|---|---|---|
| 5,814,729 | A * | 9/1998 | Wu | G01M 5/0033 356/32 |
| 6,065,342 | A * | 5/2000 | Kerr | G01N 29/14 367/127 |
| 6,076,405 | A * | 6/2000 | Schoess | G01H 1/003 73/587 |
| 6,378,387 | B1 * | 4/2002 | Froom | G01M 5/0016 73/865.8 |
| 6,628,567 | B1 * | 9/2003 | Prosser | G01H 1/00 367/13 |
| 7,131,331 | B2 * | 11/2006 | Bates | G01N 25/72 73/589 |
| 7,375,801 | B1 * | 5/2008 | Briscoe | G01C 3/08 356/3.1 |
| 7,516,663 | B2 | 4/2009 | Ringermacher et al. | |
| 8,483,977 | B1 * | 7/2013 | Johnnie | G01N 29/0609 702/36 |
| 2006/0004499 | A1 * | 1/2006 | Trego | B64D 45/00 701/31.4 |
| 2006/0095199 | A1 * | 5/2006 | Lagassey | G07C 5/008 701/117 |
| 2006/0283262 | A1 * | 12/2006 | Smits | G01N 27/041 73/799 |
| 2007/0223557 | A1 * | 9/2007 | Pevzner | G01N 25/72 374/5 |
| 2007/0282541 | A1 * | 12/2007 | Griess | H04Q 9/00 702/34 |
| 2008/0105055 | A1 * | 5/2008 | Ringermacher | G01N 23/04 73/643 |
| 2008/0183403 | A1 * | 7/2008 | Cipra | G01M 5/0025 702/34 |
| 2008/0307886 | A1 * | 12/2008 | Marsh | G01N 29/223 73/601 |
| 2009/0070048 | A1 * | 3/2009 | Stothers | G01N 29/045 702/39 |
| 2010/0019153 | A1 * | 1/2010 | Zalameda | G01N 25/72 250/339.02 |
| 2010/0238027 | A1 * | 9/2010 | Bastianini | G01D 9/005 340/540 |
| 2011/0054806 | A1 * | 3/2011 | Goldfine | G07C 3/00 702/34 |
| 2011/0144930 | A1 * | 6/2011 | Bruno | G01S 3/801 702/56 |
| 2012/0253707 | A1 * | 10/2012 | Qi | G01N 29/043 702/56 |
| 2012/0320372 | A1 * | 12/2012 | Troy | G01N 29/043 356/237.2 |
| 2015/0035950 | A1 * | 2/2015 | Kontsos | G01N 29/14 348/47 |
| 2015/0215584 | A1 * | 7/2015 | Tapia | G01N 21/8851 348/125 |
| 2015/0253266 | A1 * | 9/2015 | Lucon | G01N 25/72 374/4 |
| 2017/0234837 | A1 * | 8/2017 | Hall | G01N 29/2431 73/602 |

OTHER PUBLICATIONS

Oxford Dictionary, definition of resolution (Year: 2016).*
Zalameda et al., "Real time fatigue damage growth assesment of a composite three stringer panel using passive thermography," 2015 SPIE Thermosense Conference; Apr. 20-24, 2015, Baltimore, MD.

* cited by examiner

SYSTEM AND METHOD FOR PROGRESSIVE DAMAGE MONITORING AND FAILURE EVENT PREDICTION IN A COMPOSITE STRUCTURE

CROSS-REFERENCE TO RELATED PATENT APPLICATIONS

This patent application claims the benefit of and priority to U.S. Provisional Patent Application No. 62/207,593 filed on Aug. 20, 2015, and U.S. Provisional Patent Application No. 62/315,363 filed on Mar. 30, 2016, the contents of which are hereby incorporated by reference in their entirety.

STATEMENT REGARDING FEDERALLY SPONSORED RESEARCH OR DEVELOPMENT

The invention described herein was made in the performance of work under a NASA contract and by employees of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor elected not to retain title.

TECHNICAL FIELD

The present disclosure relates to the monitoring of damage progression and prediction of a failure event in a composite structure.

BACKGROUND OF THE INVENTION

Aircraft components such as fuselages, wings, stabilizers, landing gear doors, and flight control surfaces are traditionally constructed of aluminum alloy or other lightweight metals. In order to further reduce weight, increase strength, improve corrosion resistance, and provide other attendant benefits, such components may be alternatively constructed from advanced composite materials. Examples of such advanced composite materials include carbon laminates and carbon sandwich composites, as well as woven or non-woven materials such as KEVLAR, boron, graphite, and fiberglass.

Damage modes for composite structures include delamination/de-bonding, fiber breakage, and matrix cracking. In-situ inspection may be necessary due to the potential for damage to progress due to handling and testing of the composite structure. Fatigue testing of such composite structures is critical to the validation of structural designs and programming of damage prediction models, which require an accurate understanding of the formation and growth of damage so that failure of the composite structure may be accurately predicted.

Conventional inspection methodologies include acoustic emission testing, passive thermography, digital image correlation, and fiber optic sensing. Acoustic emission testing involves the use of sensitive acoustic emission sensors to locate acoustic events. The acoustic events, which are caused by micro-level and macro-level changes in the composite structure, may be associated with certain types of damage. Acoustic emission testing is generally able to detect damage onset, but cannot optimally detect the shape, size, and depth of such damage. However, all sources of acoustic emission do not develop into critical damage.

Passive thermography is a non-contact inspection method that uses infrared cameras to detect localized areas of heating. Such heating can be caused by breaking, rubbing, or clapping together of materials in the damaged areas, and can provide additional information regarding damage location and size. Digital image correlation measures displacement at the surface due to damage under loading, but requires significant amounts of subsurface damage to accumulate before being detectable at the surface. Fiber optic measurement can detect changes in strain in a test sample, but likewise is relatively ineffective in measuring the shape or depth of damage.

Systems and methodologies exist for detecting and quantifying failure events using a combination of sensor technologies of the types described above. For instance, U.S. Pat. No. 7,516,663 to Ringermacher et al. discloses a process for locating a failure event via acoustic emission sensors. Time-based thermography data is then used to study the area of the detected emission event and track the evolution of heat at the location so as to determine a depth of any damage. However, while such an approach takes advantage of the different capabilities of acoustic and infrared sensors, it remains less than optimal for use in wide area in-situ fatigue monitoring in loaded composite structures, as well as for accurately predicting composite failure.

BRIEF SUMMARY OF THE INVENTION

A system and method are disclosed herein that are suitable for wide area, in-situ measurement of progressive damage in a loaded composite structure, as well as for predicting a failure event. The composite structure may be a panel of an aircraft in some embodiments, for instance a panel or other portion of a fuselage, wing, stabilizer, door, flight control surface, or other structural element, with loading of the composite structure being indicative of expected forces such as engine vibration, wind resistance, and/or twisting. As part of the present approach, an array of acoustic emission sensors are acoustically coupled to the composite structure and used by one or more computer devices, referred to herein collectively as a programmable monitoring device, to detect damage in a two-dimensional (2D) plane. A damage-free composite structure should not return an acoustic signature, while a damaged structure often produces sound that tends to become more pronounced as the damage worsens. Because the respective 2D position of each acoustic emission sensor is known, the position of any detected acoustic event may be determined by the monitoring device via triangulation or using other calculations.

An ultimate goal of the present approach is to detect damage in the composite structure when the composite structure is subjected to a load, and to thereafter synchronously use imagery from a camera, e.g., one or more infrared or visible spectrum cameras, to closely track damage progression while the composite structure remains subjected to the load. Damage progression can be closely tracked and recorded in memory of the programmable monitoring device, i.e., any computer or computer programmed to execute the disclosed methodology and having a processor, sufficient memory, and image processing instructions as set forth herein. Over time, the recorded damage progressions can be fed into a failure model and used in real time, e.g., by a maintenance system aboard an aircraft, watercraft, spacecraft, land-based craft, or other top-level mobile or stationary system to predict where and when similar failures may develop, thereby prompting corrective or preventative action with sufficient lead time.

In a particular embodiment, a system for monitoring damage progression in a composite structure includes one or more load sensors, an array of acoustic emission sensors, one or more cameras, and a programmable monitoring device of the type noted above. The load sensor is operable for measuring an applied load to the composite structure, such as vibration energy, twisting deformation, or a constant or intermittent linear force, and outputting a load profile signal corresponding to or indicative of the measured applied load. The acoustic sensors, which are configured to acoustically couple to the composite structure, are operable for measuring acoustic emission data when the load is applied to the composite structure. The camera captures image data of the composite structure in a designated portion of the electromagnetic spectrum, e.g., the infrared or visible light spectrum.

The monitoring device, which is in communication with the load sensor, the acoustic emission sensors, and the camera, is programmed to synchronously measure all of the applied load via the load sensor, the acoustic emission data, and the image data, such that a given image, with its above-noted ability to determine the damage location and size, can be correlated with the applied load and acoustic emission data collected at the point in time of the synchronous measurement. The monitoring device is also programmed to automatically map the collected acoustic emission data onto the collected image data to detect an area of damage progression in the composite structure, with the monitoring device ultimately correlating such mapped data to the applied load in executing various possible control actions, some examples of which are set forth herein.

A method for monitoring damage progression in a composite structure is also disclosed. The method may include measuring acoustic emission data, via an array of acoustic emission sensors each acoustically coupled to the composite structure, when the composite structure is subjected to the applied load. The method may also include synchronously collecting image data via a camera in a designated portion of the electromagnetic spectrum, and measuring the applied load via a load sensor while synchronously collecting the acoustic emission data and the image data. Additionally, the method includes automatically mapping the collected acoustic emission data onto the collected image data via a programmable monitoring device to thereby detect an area of damage progression in the composite structure corresponding to the applied load.

The above features and advantages and other features and advantages of the present disclosure are readily apparent from the following detailed description of the best modes for carrying out the disclosure when taken in connection with the accompanying drawings.

DETAILED DESCRIPTION

Figure 1:
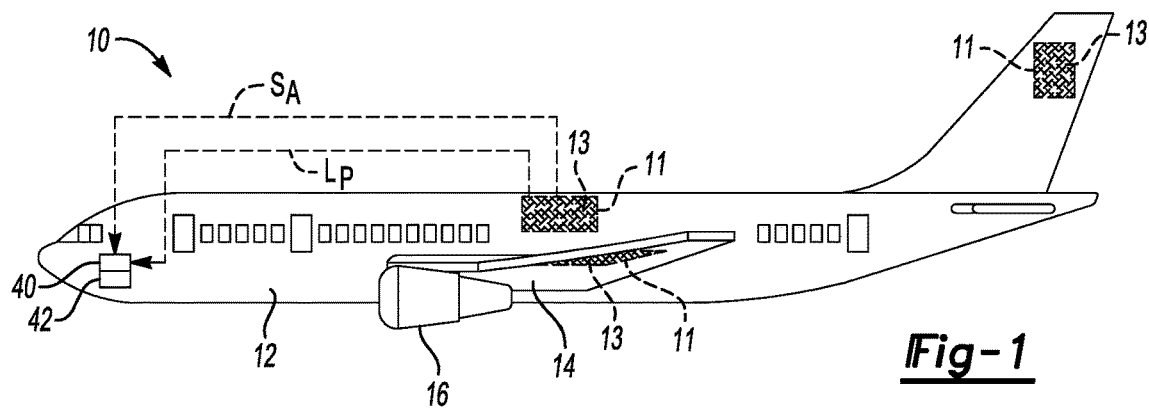
FIG. 1 is a schematic side view illustration of an example aircraft having a composite structure that can be monitored using the method set forth herein.

Referring to the drawings, wherein like reference numbers refer to the same or similar components in the various Figures, an example aircraft 10 is shown schematically in FIG. 1. The aircraft 10 is constructed using composite structures 11 constructed of advanced composite materials 13, e.g., one or more panels, outer skins, or other components used as part of a fuselage 12 or wings 14, or flight control surfaces, landing gear doors, fairings, stabilizers, and internal components such as floors and bulkheads, not all of which are shown in FIG. 1 but all of which are well known in the art. While the aircraft 10 is described herein as being representative of the type of structure that would benefit from use of the composite structure 11, other structural systems or components such as boats or other marine platforms, aerospace platforms, land-based or terrestrial vehicles, and stationary platforms may be contemplated within the scope of the present disclosure. For illustrative consistency, the aircraft 10 will be described hereinafter in conjunction with the composite structure 11 without limiting the scope of the disclosure to the aircraft 10 of FIG. 1 or aerospace applications in general.

Each wing 14 of the aircraft 10 may be connected to one or more engine assemblies 16. The engine assemblies 16 act as sources of vibration and thus load the composite structure 11 of the aircraft 10 when the aircraft 10 is in operation. Other sources of loading on the fuselage 12, wing 14, and other structure of the aircraft 10 may include wind resistance and transient or sustained torsional/twisting forces imparted to the aircraft 10 as the aircraft 10 taxis down a runway or maneuvers through the air while in flight.

Due to the relatively recent adoption of advanced composite materials 13 in the construction of aircraft such as the example aircraft 10 of FIG. 1, failure modes and damage progression in composite materials 13 are not as well understood as those constructed, for instance, using conventional aluminum alloys. Therefore, the present disclosure is intended to provide a workable methodology for performing, wide area measurement of damage initiation and progression in a test sample of the composite structure 11 when the composite structure 11 is subjected to an applied load, indicated via an arrow "LOAD" in FIGS. 2A and 2B. The applied load is typical of the type of loading expected to be experienced by the composite structure 11 due to forces acting on the composite structure 11 during operation, e.g., of the aircraft 10 or other system in which the composite structure 11 is used.

Figure 2A:
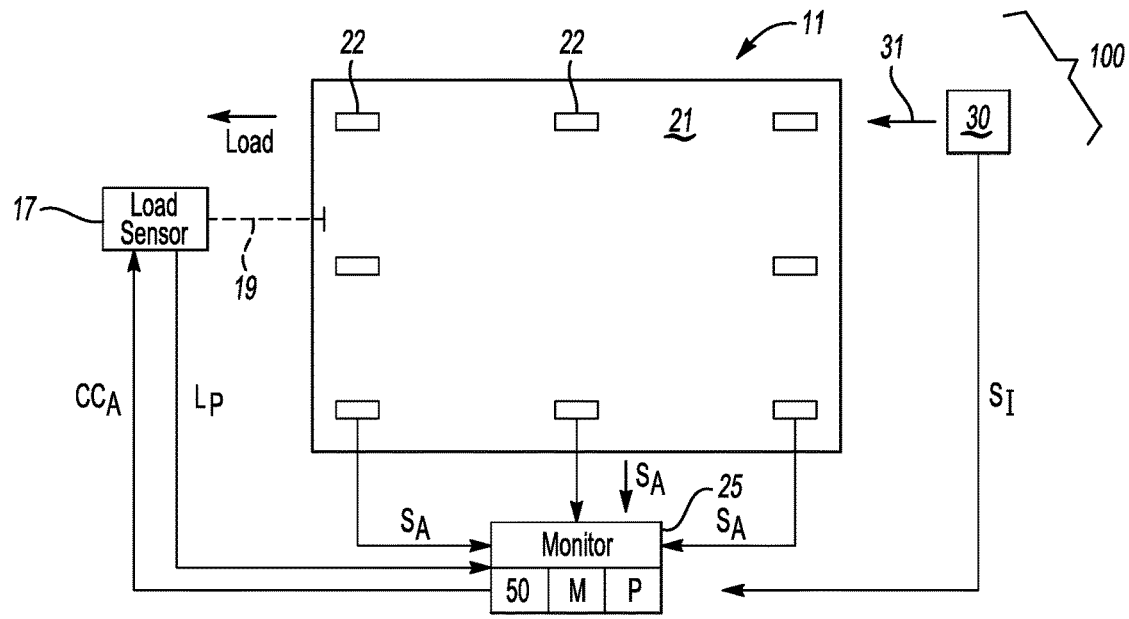
FIGS. 2A and 2B are a pair of schematic illustrations of an example system for performing wide-area, in-situ monitoring of damage progression in a composite structure.
Figure 2B:
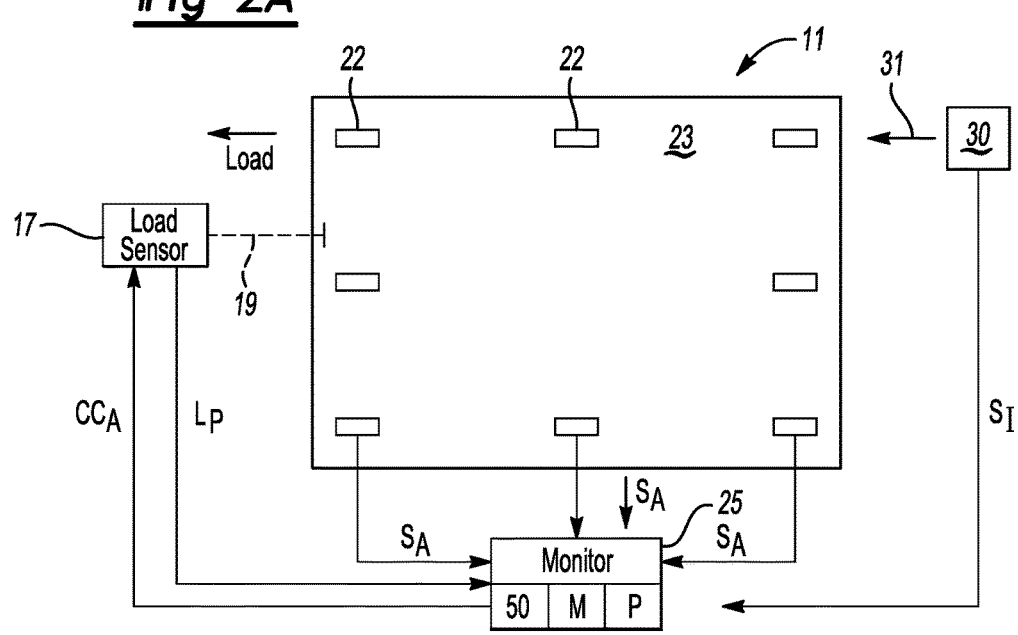

The present disclosure also pertains to the prediction of location/position and time of failure in the loaded composite structure 11, with possible real-time applications of the collected test data as set forth herein. For instance, load sensors 17 and acoustic emission sensors 22 as shown in FIGS. 2A-2B may be positioned with respect to, embedded in, and/or connected to the composite structure 11 of FIG. 1, e.g., as thin-film microsensors or transducers, to continuously measure the applied load and transmit the load profile signal (arrow $L_P$) corresponding to the applied load, as well as to transmit the acoustic emission signals (arrow $S_A$), to a maintenance system 40 or other computer device positioned in an accessible location in the aircraft 10. Using a failure prediction model 42 informed via the acoustic, load, and image data collected via the respective acoustic emission sensors 22, load sensors 17, and cameras 30 as set forth below with reference to FIGS. 2A-5B, the maintenance system 40 may be optionally programmed to generate real-time alerts or execute other possible control actions when a particular damage acoustic and thermal profile is detected for a given applied load as experienced during actual operation of the aircraft 10.

Referring to FIGS. 2A-2B, an example system 100 is shown that may be used to conduct wide area, in-situ, nondestructive evaluation (NDE) inspections of the composite structure 11, shown in this particular non-limiting example as a relatively flat composite panel. The system 100 may be used for fatigue testing of the composite structure 11 in order to track damage initiation and growth. The present approach considers the progression of damage of the type potentially leading to an ultimate failure in the composite structure 11 in order to validate and implement damage progression models, e.g., the real-time damage prediction model 42 shown schematically in FIG. 1. In a particular embodiment, the method 100 combines passive thermography or other imaging and acoustic emission NDE in order to track damage growth up to the point of a failure event in the composite structure 11.

FIG. 2A depicts an array of acoustic emission sensors 22, each of which is acoustically coupled to the composite structure 11 and possibly amplified, for instance via a multi-channel amplifier (not shown). For the purposes of NDE testing, the composite structure 11 may be a full composite panel or component, or a smaller test sample portion thereof. The acoustic emission sensors 22 may be embedded in the material of the composite structure 11, or they may be taped or otherwise affixed to a first surface 21 of the composite structure 11. The acoustic signals (arrows $S_A$) from the various acoustic emission sensors 22 are then acquired simultaneously, i.e., all of the sensors 22 operate at the same time. The acoustic emission sensors 22 each have known/calibrated XY coordinates providing a reference 2D position, programmed into memory (M) of a controller or monitoring device (C) 25, such that the 2D position of detected damage in the composite structure 11 can be triangulated via the monitoring device 25 as is well known in the art.

In addition to the acoustic emission sensors 22, the system 100 also includes one or more cameras 30 orientated in a direction facing the composite structure 11, with such orientation indicated in FIGS. 2A and 2B by arrow 31. As used herein, the term camera refers to any device capable of collecting electro-optical image data (arrow $S_I$) in any designated range of the electromagnetic spectrum. Each camera 30 is operable for capturing the image data (arrow $S_I$) of an area or cluster 27 (see FIGS. 5A and 5B) of detected threshold damage from the array of acoustic emission sensors 22. As used herein, the image data (arrow $S_I$) may be any imagery ranging from the ultraviolet to the infrared, i.e., having wavelengths of about 0.25 μm, through the visible spectrum, and to the limits of the infrared region, e.g., about 14 μm or more.

In a particular embodiment, the cameras 30 may include multiple cameras oriented, e.g., a first camera 30 facing a first surface 21 of the composite structure 11 as shown in FIG. 2A, e.g., a flat side of a composite fuselage panel, and a second camera 30 oriented facing a second surface 23 of the composite structure 11 as shown in FIG. 2B, e.g., a stringer side of a composite fuselage panel. The cameras 30 may be embodied as infrared (IR) cameras in a particular embodiment, i.e., operable for collecting thermographic images in a particular short, medium, or long range IR band of the electromagnetic spectrum. Alternatively, the cameras 30 may be operable for collecting imagery in the visible spectrum, typically about 0.40 to 0.70 μm.

As part of the system 100, the composite structure 11 is also mechanically coupled or in wireless or wired communication with one or more load sensors 17, with the physical or wireless interconnection between the load sensors 17 and the composite structure 11 schematically represented in FIGS. 2A-2B via connection 19. As is known in the art, such an applied load may be imparted during controlled testing via a load frame and hydraulic actuators (not shown) capable of inputting a cyclical compressive load to the composite structure 11 with a predetermined frequency and amplitude, or may represent real-time loading of the aircraft 10 or other system in actual operation.

The load sensor 17 is operable for measuring the applied load to the composite structure 11 and outputting an electrical signal describing the applied load as the load profile signal (arrow $L_P$). The load sensor(s) 17 may be variously embodied as accelerometers, strain gauges, fiber optic sensors, laser or other displacement sensors, or load cells. In some embodiments, the load sensor 17 may be configured to remotely sense a displacement of the composite structure 11 in response to the applied load. For instance, a laser sensor may be used to remotely measure linear displacement or deformation of the composite structure 11.

The camera(s) 30 in all embodiments are operable for collecting image data (arrow $S_I$) of the composite structure 11 during sustained loading. The load profile signal (arrow $L_P$) is measured simultaneously with collection of the acoustic emission signals (arrows $S_A$), the latter of which are then automatically mapped via the monitoring device 25 directly onto one or more of the collected images embodying the image data (arrow $S_I$) so as to confirm the existence of areas of damage growth that may potentially lead to a failure event in the composite structure 11, as opposed to any detected acoustic event. This requires the careful synchronization of the acoustic emission data (arrow $S_A$) and image data (arrow $S_I$) with applied loading. Additionally as set forth below with reference to FIG. 4, the method 50 may include an imaging processing subroutine 60 that in turn includes pre-processing the collected image data (arrow $S_I$) through the steps of contrast enhancement, removal of optical barrel distortion, and correction of angular rotation before mapping of the acoustic event locations.

The monitoring device 25 used to execute the method 50 as part of the system 100 includes a processor (P) and the memory (M), such as magnetic or optical read-only memory, along with other requisite hardware, e.g., input/output devices and a display screen or other indicator. The memory (M) includes random access memory and programmable read-only memory, with the latter programmed with computer-readable instructions describing the method 50 for performing the disclosed monitoring functions for determining and tracking damage progression in the composite structure 11, as well as ultimately predicting a failure event in the composite structure 11. A non-limiting example embodiment of the method 50 is depicted in FIG. 4 and described below, with elements of the method 50 further described with reference to FIG. 3.

Figure 5B:
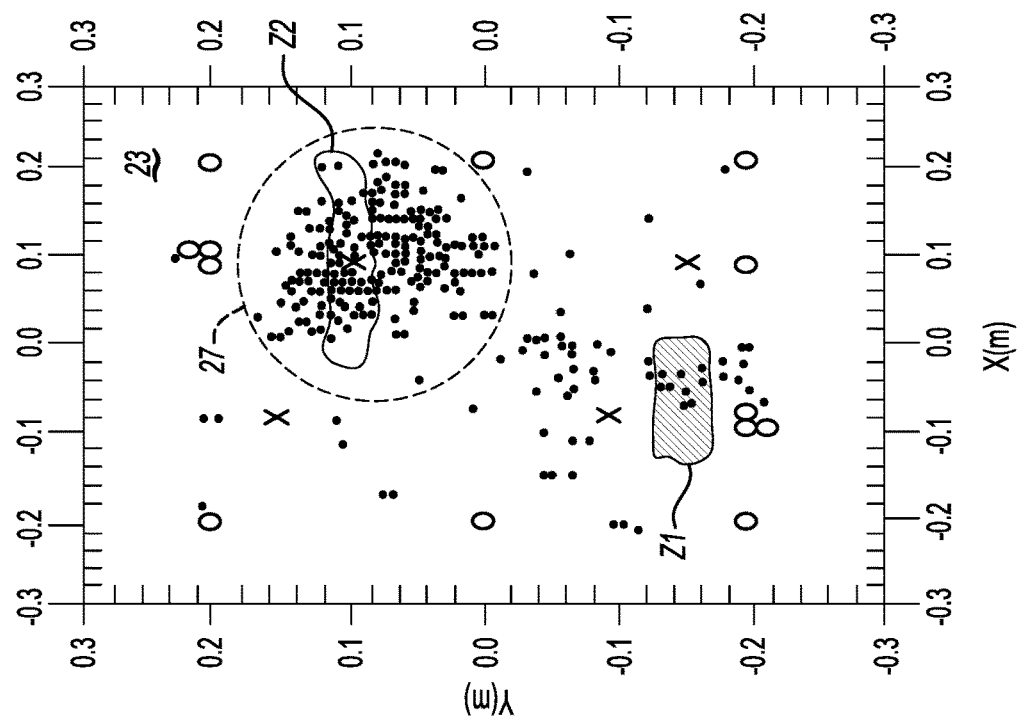
FIGS. 5A and 5B are schematic illustrations of representative acoustic emission and thermal events in a composite panel.
Figure 5A:
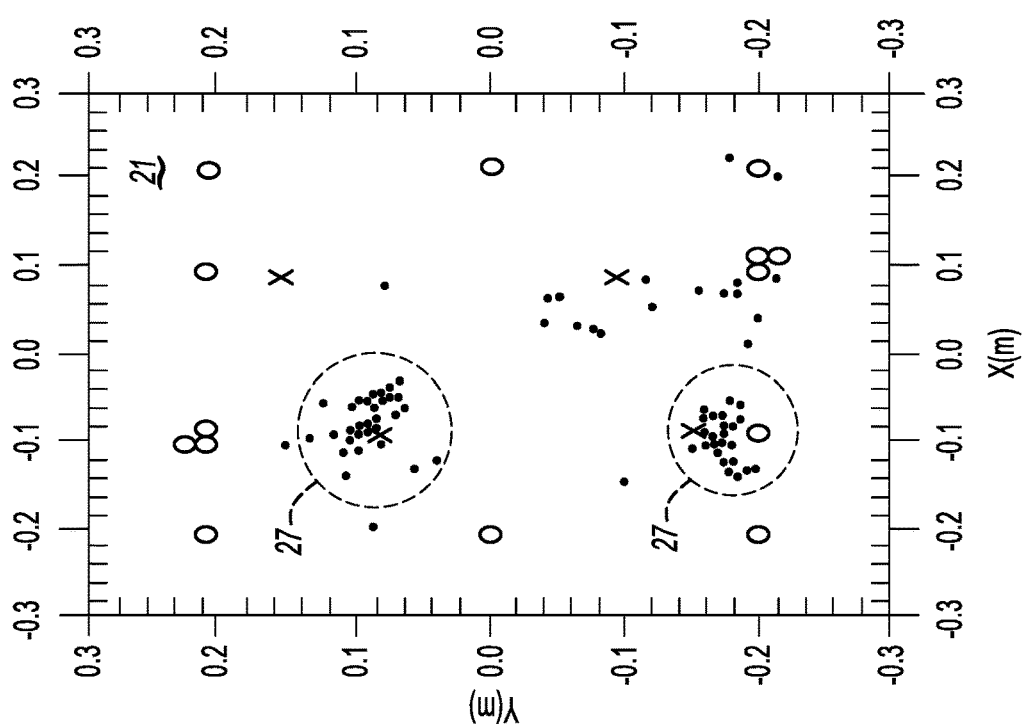

Referring briefly to FIGS. 5A and 5B, two plots are shown of the composite structure 11, with its representative vertical/Y(m) axis and horizontal/X(m) axis represented in meters (m). FIGS. 5A-5B depict representative impact events (X), which may be artificially generated impact events intended to initiate damage for the purpose of studying damage progression. Also depicted are the triangulated 2D locations of acoustic emission events (·) from the acoustic emission sensors 22, i.e., incidences of acoustic detection by the sensors 22. The locations of the acoustic emission sensors 22 are indicated via the character "o".

FIG. 5A depicts the first surface 21 at about 97.3% of its useful life. FIG. 5B depicting the second surface 23 at about 99.9% of its useful life without thermal data. FIGS. 5A-5B illustrate the observation that, as the composite structure 11 nears ultimate failure, the accumulated acoustic events tend to increase as a function of time. Clusters 27 of acoustic events are indicative of possible areas of damage progression. Therefore, time-synchronized images of the clusters 27 or areas of damage progression used with collected image data as part of the method 50 to accurately predict the time of ultimate failure of the composite structure 11, with failure most likely to occur in areas in which the clusters 27 appear in close conjunction with any validating thermal or visible spectrum imagery confirming the damage progression.

For instance, FIG. 5B depicts example zones Z1 and Z2, which are areas in which heating is detected by the cameras 30 shown in FIGS. 2A and 2B. Zone Z1 illustrates a situation in which heating is detected without detected damage growth. Such a zone Z1 is indicative of an area that, in spite of impact events being present in that area of surface 23, damage is not progressing appreciably. Zone Z2 by contrast indicates substantial heating and damage growth. This is confirmed by the clustering of acoustic emission event locations. Thus, the detected heating and acoustic emission information can be correlated with the measured applied load such that, when similar loads are experienced and similar acoustic and heating information presents itself, accurate predictions may be made as to where and when a failure is likely to occur.

Figure 3:
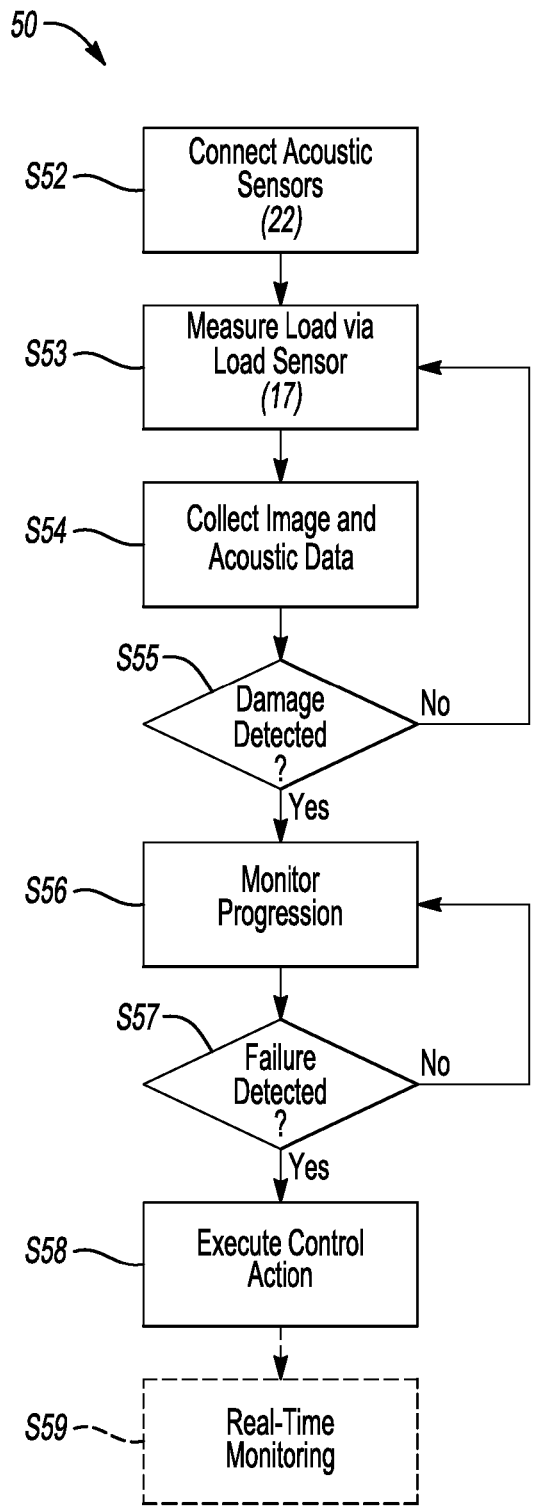
FIG. 3 is a flow diagram describing an example method of using the system shown in FIGS. 2A-2B.
Figure 4:
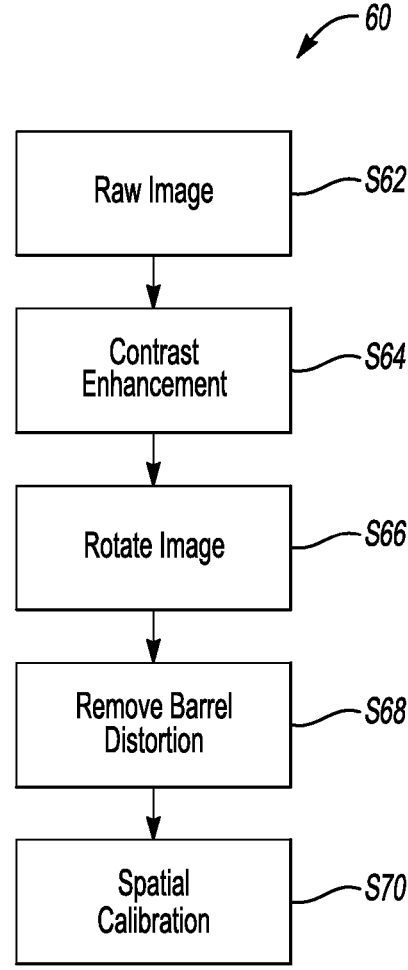
FIG. 4 is a flow diagram describing the processing of collected imagery data as part of the method depicted in FIG. 3.

FIG. 3 depicts an example embodiment of the method 50. Beginning with step S52, a plurality or array of the acoustic emission sensors 22 of FIGS. 2A and 2B are positioned with respect to the composite structure 11 such that the acoustic emission sensors 22 are acoustically coupled to the composite structure 11. While eight such acoustic emission sensors 22 are depicted in FIGS. 2A-2B, any number of acoustic emission sensors 22 may be used. Generally, it may be advantageous to place acoustic sensors 22 outside of the immediate field of view of the cameras 30 so that thermal or other image data can be accurately read. Step S52 includes connecting the acoustic emission sensors 22 in a particular array or pattern on the composite structure 11, such as equally spacing the acoustic emission sensors 22 on the opposite first and second surfaces 21 and 23 of the composite structure 11 as shown in FIGS. 2A and 2B, respectively. The 2D position or coordinates of each acoustic emission sensor 22 is then recorded in memory (M) of the monitoring device 25 to enable later triangulation of any detected acoustic emission event. The method 50 then proceeds to step S53.

At step S53, the monitoring device 25 measures the applied load to the composite structure 11 via the load sensor 17. The load sensor 17 then transmits the load profile signal (arrow $L_P$) to the monitoring device 25 to inform the monitoring device 25 of the measured applied load. The method 50 then proceeds to step S54.

Step S54 includes collecting the acoustic emission data (arrow $S_A$) and the image data (arrow $S_I$) in a time-synchronized manner. That is, the cameras 30 synchronously collect the image data (arrow $S_I$) with collection of the acoustic emission data (arrow $S_A$), with the acoustic emission data (arrow $S_A$) ultimately used by the monitoring device 25 to triangulate or otherwise determine the 2D position of any incident damage in the composite structure 11 as explained above. This occurs while the composite structure 11 remains under load.

As is known in the art, acoustic emission systems such as the array of acoustic emission sensors 22 shown in FIGS. 2A-2B are able to collect structure-borne sound in the ultrasonic frequency band, or approximately 50-500 kHz. Such inaudible sound is generated by small-scale damage initiation and growth. Pre-cursors to ultimate failure of the composite structure 11 are then closely monitored in real-time. Further to this analysis, the total signal energy (SE) of an acoustic signal such as the acoustic emission data (arrow $S_A$) may be represented mathematically as:

$$SE = \Sigma_{i=1}^{n} V^2 \Delta t$$

where V is the signal voltage, i is the time reference point, n is the number of time data points in the acoustic emission data (arrow $S_A$), and $\Delta t$ is the sampling time per data point. Trends in the signal energy (SE) over time are then able to be used by the monitoring device 25 to identify and track damage development, such as matrix cracks, fiber breaks, or delamination. Signals from the distributed array of acoustic emission sensors 22 are acquired simultaneously when any one acoustic emission sensor 22 detects a calibrated threshold amount of sound, which allows calculation via triangulation of the 2D position of the damage event.

Part of step S54 includes mapping, via the monitoring device 25, the collected acoustic emission data (arrow $S_A$), which is performed directly onto the time-synchronized images from the captured image data (arrow $S_I$). As part of this process, delayed image subtraction may be used to improve defect contrast in the processed image data (arrow $S_I$). A moving buffer may be implemented in image acquisition software of the monitoring device 25. Delayed subtraction may be given as:

$$\text{Difference Image} = \text{Acquired Image}[i] - \text{Previous Image}[i-k/2]$$

where k is the number of images per cycle and i is the current acquired image number. Dividing the factor k by 2 ensures that the maximum and minimum temperature images are subtracted within a given cycle. This provides a series of useful images with optimal defect contrast varying with image depth. Improved defect signal-to-noise can be obtained by averaging the difference images over a number of cycles if so desired.

Referring briefly to FIG. 4, an imaging processing subroutine 60 may be used as part of the method 50 to map the collected acoustic emission data (arrow $S_A$) onto the collected imagery data (arrow $S_I$). Step S62 includes collecting the raw image data (arrow $S_I$), then improving image contrast at step S64 as explained above. Step S66 includes rotating the improved image to remove angular rotation. For instance, step S66 may include using affine transformation, e.g., translation or scaling.

After completing step S66, step S68 is executed to remove any optical barrel distortion, e.g., via an image forward transformation given by the following equation:

$$r_{undistorted} = r_{distorted}(1 - d(r_{distorted})^2)$$

where $r_{undistorted}$ is the corrected Cartesian coordinate vector distance from the center of the improved collected image and $r_{distorted}$ is the distorted Cartesian vector distance from the center of the collected image. The parameter d may be set as needed to remove the distortion, e.g., d=0.2 in one possible application.

Additionally, at step S70 the image data is spatially calibrated, e.g., resolution per pixel is determined by measuring known distances on the composite structure 11. Exemplary pixel resolution in a thermal image is 8.2 pixels per cm. Acoustic emission data (arrow $S_A$), such as shown in FIGS. 5A and 5B described above, can then be mapped onto the image data (arrow $S_I$) as processed by the imaging processing subroutine 60 of FIG. 4 in order to reveal clustering of acoustic emission event locations around image signatures of interest, e.g., thermal signatures.

Referring again to FIG. 3, step S55 of method 50 includes detecting an area of damage on the mapped acoustic emission and image data from step S54. Step S53 is repeated if such damage is not detected. The method 50 proceeds to step S56 when damage is detected. At step S55 and prior, both the received image data (arrow $S_I$) and the acoustic emission data (arrow $S_A$) is time-synchronized to each other and to the measurement of the applied load by the load sensor 17. Therefore, acoustic emission events are temporally matched to the images in the image data (arrow $S_I$).

Optionally, for a given damage position, the monitoring device 25 may map an indicator based on total energy in the various detected acoustic emission events. That is, a control action may be executed that includes displaying a graphical indicator indicative of the total energy level of the acoustic emission event on an image of the composite structure 11, doing so via the monitoring device 25, e.g., via a display screen. The color, size, and/or opacity of the graphical indicator displayed via the monitoring device 25 may correspond to the total energy level.

For instance, using the relationship Indicator=Round [(event energy)$^{1/4}$+10] where the event indicator value of less than 13 (e.g., with a minimum size of 10) may be given a low-energy color, e.g., blue with an opacity of 0.5, indicator values between 13 and 15 may be designated as mid-energy events and given another color, e.g., yellow with an opacity of 0.7, and indicator values greater than 15 may be designated a high-energy event with another color, e.g., red with an opacity of 1. Thus, the zones Z1 and Z2 could have different color-coded energy levels in some embodiments to facilitate rapid human or machine analysis.

At step S56, the monitoring device 25 next monitors the progression of the damage detected at step S55. As the composite structure 11 approaches failure, the accumulated acoustic events and indicator values will increase. Ultimate failure may occur in an area of the composite structure 11 where the high-energy and mid-energy indicators become clustered. It is important to note that the location of the acoustic emission events may be prone to some amount of error due to the progression of damage as the composite structure 11 nears failure. Defects can affect the velocity and waveform mode of propagation of acoustic emission signals (arrow $S_A$), resulting in processing errors. However, the clustered positions remain as valid indications of areas of growing damage.

To facilitate the mapping of data, the method 50 may optionally include tailoring or adjusting the resolution or frame rate of the camera(s) 30 to a level or severity of detected acoustic emission events, i.e., the greater the number and/or amplitude of acoustic events in a given area, for a given load, the more images the camera 30 may collect of that particular area. Thus, the monitoring device 25 may be optionally configured to control a resolution of the camera 30 in a targeted area of the composite structure 11 based on a level of the acoustic emission event, e.g., as a predetermined function of a concentration, amplitude, or severity of the acoustic emission data in the targeted area. The additional images from the camera 30 may be stored in a buffer to improve time resolution of the mapped data in the particular area. In other words, a property of the acoustic emission events indicative of severity, e.g., a number or concentration of acoustic events, may be used as a control input in the overall resolution control of the camera 30.

Step S57 includes predicting or detecting, using the mapped acoustic emission and image data, a failure event in the areas of damage progression as monitored in step S56. Step S57 may include detecting an actual failure as set forth above, or it may include projecting a rate of damage progression forward in time to predict when such a failure might be expected to occur. As part of step S57, when damage growth is detected, controlled loading via a load frame (not shown) may be temporarily stopped by operation of the monitoring device 25 of FIGS. 2A and 2B to allow for more detailed localized inspection, e.g., using x-ray imaging, non-immersion ultrasound imaging, or flash inspection of the composite structure using flash heating lamps. Such techniques may provide a detailed assessment of damage growth through the thickness of the composite structure 11 and thus ultimately provide a better understanding of damage progression modes that can lead to ultimate failure. The progression of damage in between such validation measurements can be recorded in the monitoring device 25 to document failure.

At step S58, the monitoring device 25 executes a control action with respect to the composite structure 11 in response to the detected or predicted failure event. A possible control action includes the recording of the time of the detected or predicted failure event in memory (M) of the monitoring device 25, along with the 2D position or positions of the initial damage or clusters 27. Over time, a more diverse set of fatigue monitoring data may be recorded in memory (M) to provide a more thorough understanding of the failures modes of the composite structure 11, with possible real-time applications.

That is, additional control actions may include real-time control actions using the maintenance system 40 shown in FIG. 1, e.g., as step S59. For instance, the maintenance system 40 may be programmed with the failure prediction model(s) 42 noted above, which themselves can be populated with detected or predicted failure event data from the method 50 for a given actual load or range of actual loads. That is, the monitoring device 25 may be placed in communication with the maintenance system 40, or data from the memory (M) of the monitoring device 25 may be downloaded to memory of the maintenance system 40. The maintenance system 40 of FIG. 1 is thereby made aware of past damage patterns and past loads corresponding to such patterns that, as confirmed by the monitoring device 25 using the cameras 30 and the method 50, ultimately resulted in an actual or predicted failure event.

Once the maintenance system 40 is so programmed, the array of acoustic emission sensors 22 and one or more of the load sensors 17 may be used to respectively measure acoustic emission signals (arrow $S_A$) aboard the aircraft 10 and the load profile signal (arrow $L_P$) in real time, and to transmit the measured acoustic emission signals (arrow $S_A$) and the load profile signal (arrow $L_P$) to the maintenance system 40. Using the failure prediction model(s) 42 and the received acoustic emission signals (arrow $S_A$), the maintenance system 40 can detect, once again in real time, whether similar damage clusters to the damage clusters 27 previously detected and validated for similar loads via synchronized thermography or other imaging are present. If so, the maintenance system 40 may activate an indicator, e.g., a lamp, and/or record a diagnostic code signaling for closer ultrasonic or x-ray inspection of the composite structure 11, and possible replacement of sections of the composite structure 11.

Using the system 100 described above, both acoustic emission events and thermal, visible, or other imagery events are time-synchronized to loading on the composite structure 11 to improve how acoustic and image-based indications are processed and interpreted. As heat may be present without structural damage, e.g., due to radiated heat from a proximate component, and as some amount of damage may be present without generation of significant heat, the present approach monitors both the acoustic emission events and image-based events, synchronized to each other and to loading, so as to correlate the image data with actual structural damage, as well as to track damage progression. The method 50 allows heating trends to be identified in conjunction with clustered acoustic emission events and plotted as accumulated energy and related thermography or other image curves, e.g., temperature vs. time or area pixel vs. time above a calibrated threshold, so as to reveal where the composite structure 11 is likely to fail, as well as to enable any false indications to be disregarded.

Because the method 50 maps acoustic emission events to thermography or other images, multiple damage sites can be closely tracked as damage is permitted to grow in a controlled manner. As a result, large area NDE capability is made possible for accurately determining damage onset and growth in composite structures under sustained load testing. The designing, construction, and testing of more advanced complex composite structures 11 is thereby enabled.

While the best modes for carrying out the disclosure have been described in detail, those familiar with the art to which this disclosure relates will recognize various alternative designs and embodiments for practicing the disclosure within the scope of the appended claims.

What is claimed is:

1. A system for monitoring damage progression in a composite structure subjected to an applied load, the system comprising:
    a load sensor operable for measuring the applied load and outputting a load profile signal indicative of the measured applied load;
    an array of acoustic emission sensors acoustically coupled to the composite structure, and each operable for simultaneously measuring acoustic emission data representing acoustic emissions from the composite structure in response to the applied load indicative of acoustic events in an area of possible damage to the composite structure, each of the acoustic emission sensors having a fixed two-dimensional coordinate associated therewith;
    a camera operable for capturing time-synchronized image data of the area of possible damage to the composite structure, in a designated portion of the electromagnetic spectrum, while the composite structure is subjected to the applied load, the time-synchronized image data being simultaneously collected with measurement of both the acoustic emission data and applied load, and containing signatures of interest indicative of the possible damage, including a size and a location of the possible damage; and
    a monitoring device in communication with the load sensor, the acoustic emission sensors, and the camera, wherein the monitoring device is configured to synchronously receive the load profile signal from the load sensor, receive the acoustic emission data from the acoustic emission sensors, and receive the image data from the camera, the two-dimensional coordinates stored in the monitoring device, the monitoring device to assign to acoustic events a signal energy indicator comprising one of a low energy indicator, a mid-energy indicator, or a high energy indicator, and to automatically map the measured acoustic emission data onto the collected image data by generating clusters of the acoustic events around the signatures of interest, to detect an increase in size of the clusters indicative of an area of damage progression in the area of possible damage by an increase in mid-energy and high energy indicators of acoustic events, predict, using the size and the location of the possible damage from the image data and a trend in total signal energy from the acoustic emission data, a time of failure of the composite structure in the area of damage progression using the time-synchronized images, and execute a control action indicative of the predicted time of failure, including generating an alert signal.

2. The system of claim 1, wherein the control action includes recording, via the monitoring device, the measured applied load and a duration between an onset of the damage and the predicted failure event.

3. The system of claim 1, further comprising: a maintenance device programmed to receive the acoustic emission data and the load profile signal, and to execute a failure prediction model to thereby predict, in real time, an occurrence of the failure in the composite structure.

4. The system of claim 1, wherein the camera is configured to capture the image data in an infrared range of the electromagnetic spectrum.

5. The system of claim 1, wherein the camera is configured to capture the image data in a visible range of the electromagnetic spectrum.

6. The system of claim 1, wherein the camera includes a first camera oriented toward a first surface of the composite structure and a second camera oriented toward a second surface of the composite structure.

7. The system of claim 1, wherein the load sensor is mechanically coupled to the composite structure.

8. The system of claim 1, wherein the load sensor is configured to remotely sense a displacement of the composite structure in response to the applied load.

9. The system of claim 1, wherein the monitoring device is configured to control a resolution of the camera in a targeted area of the composite structure as a function of a severity of the acoustic emission data in the targeted area.

10. A method for monitoring damage progression in a composite structure subjected to an applied load, the method comprising:
    measuring acoustic emission data, via an array of acoustic emission sensors each acoustically coupled to the composite structure each of the acoustic emissions sensors having a fixed two-dimensional coordinate associated therewith, the acoustic emission data representing acoustic emissions from the composite structure in response to the applied load, when the composite structure is subjected to the applied load, wherein the acoustic emission data from each of the acoustic emission sensors is simultaneously collected and is indicative of acoustic events in an area of possible damage to the composite structure;
    synchronously collecting image data of the area of possible damage via a camera in a designated portion of the electromagnetic spectrum, such that the collected image data is time-synchronized with respect to measuring the acoustic emission data, the time-synchronized image data containing image signatures of interest indicative of the possible damage, including a size and a location of the possible damage;

measuring the applied load via a load sensor while synchronously collecting the acoustic emission data and the image data, such that the applied load is time-synchronized with both the collected image data and the acoustic emission data; and automatically mapping the collected acoustic emission data onto the collected image data via a programmable monitoring device to thereby detect an area of damage progression in the composite structure corresponding to the applied load, by assigning acoustic events a signal energy indicator comprising one of a low energy indicator, a mid-energy indicator, or a high energy indicator, including generating clusters of the acoustic events around the signatures of interest, detecting an increase in size of the clusters indicative of an area of damage progression in the area of possible damage by an increase in mid-energy and high energy indicators of acoustic events, predicting a time of failure of the composite structure using the time-synchronized images using the size and the location of the possible damage from the image data and a trend in total signal energy of the acoustic emission data, and executing a control action indicative of the time of failure, including generating an alert signal.

11. The method of claim 10, wherein executing a control action includes:

displaying a graphical indicator indicative of the total signal energy on an image of the composite structure via the programmable monitoring device, with at least one of a color, a size, and an opacity of the graphical indicator corresponding to the total signal energy.

12. The method of claim 10, further comprising: controlling a frame rate or a resolution of the camera in a targeted area of the composite structure based on a level of the acoustic emission data in the targeted area.

13. The method of claim 10, further comprising:

receiving, via a maintenance device programmed with a failure prediction model, a load profile signal from the load sensor indicative of the measured applied load; and using the load profile signal, the acoustic emission data, and the failure prediction model to predict, in real time, an occurrence of a failure event in the composite structure.

14. The method of claim 10, wherein the designated range of the electromagnetic spectrum includes an infrared range of the electromagnetic spectrum.

15. The method of claim 10, wherein the designated range of the electromagnetic spectrum includes a visible range of the electromagnetic spectrum.

16. The method of claim 10, wherein automatically mapping the acoustic emission data includes using delayed image subtraction and image averaging to optimize defect contrast in the collected image data.

17. The method of claim 10, further comprising: removing optical barrel distortion from the collected image data before automatically mapping the acoustic emission data onto the image data.

* * * * *